US006376569B1

(12) United States Patent
Oxman et al.

(10) Patent No.: US 6,376,569 B1
(45) Date of Patent: *Apr. 23, 2002

(54) HYDROSILATION REACTION UTILIZING A (CYCLOPENTADIENE)(SIGMA-ALIPHATIC) PLATINUM COMPLEX AND A FREE RADICAL PHOTOINITIATOR

(75) Inventors: Joel D. Oxman, St. Louis Park; Larry D. Boardman, Shoreview, both of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 07/627,009

(22) Filed: Dec. 13, 1990

(51) Int. Cl.[7] .......................... C08F 2/50; C08G 77/08; C08G 77/12; B32B 7/12
(52) U.S. Cl. ............................ 522/29; 522/16; 522/99; 522/148; 528/15; 528/25; 528/31; 428/345; 428/343
(58) Field of Search .................. 522/8, 12, 27, 522/29, 99, 16, 148; 528/15, 25, 31; 428/345, 343

(56) References Cited

U.S. PATENT DOCUMENTS

| | | | | | |
|---|---|---|---|---|---|
| 3,159,662 A | * | 12/1964 | Ashby | .................... | 260/448.2 |
| 3,178,464 A | * | 4/1965 | Pierpoint | .................. | 260/448.2 |
| 3,220,972 A | * | 11/1965 | Lamoreaux | ................ | 260/46.5 |
| 3,313,773 A | * | 4/1967 | Lamoreaux | ................ | 260/46.5 |
| 3,410,886 A | * | 11/1968 | Joy | ........................ | 260/448.2 |
| 3,470,225 A | * | 9/1969 | Knorre | .................... | 260/448.2 |
| 3,567,755 A | * | 3/1971 | Seyfried | .................. | 260/448.2 |
| 3,814,731 A | * | 6/1974 | Nitzsche | .................... | 260/46.5 |
| 4,017,652 A | * | 4/1977 | Gruber | ........................... | 522/8 |
| 4,169,167 A | * | 9/1979 | McDowell | ..................... | 522/8 |
| 4,229,274 A | * | 10/1980 | Carlblom | ....................... | 522/8 |
| 4,243,718 A | * | 1/1981 | Murai et al. | ................. | 428/411 |
| 4,276,252 A | * | 6/1981 | Kreis et al. | .................. | 264/222 |
| 4,288,345 A | * | 9/1981 | Ashby et al. | ........... | 252/431 R |
| 4,347,111 A | * | 8/1982 | Gehlhaus et al. | ............... | 522/8 |
| 4,510,094 A | * | 4/1985 | Drahnak | ............... | 260/429 CY |
| 4,530,879 A | * | 7/1985 | Drahnak | ...................... | 428/352 |
| 4,587,137 A | * | 5/1986 | Eckberg | ........................ | 522/29 |
| 4,603,168 A | * | 7/1986 | Sasaki et al. | .................. | 522/18 |
| 4,603,215 A | * | 7/1986 | Chandra et al. | ............. | 556/136 |
| 4,640,939 A | * | 2/1987 | Cavezzan et al. | .............. | 522/99 |
| 4,670,531 A | * | 6/1987 | Eckberg | ....................... | 528/15 |
| 4,699,813 A | * | 10/1987 | Cavezzan | ................... | 427/387 |
| 4,705,765 A | * | 11/1987 | Lewis | ........................ | 502/152 |
| 4,712,092 A | * | 12/1987 | Boldridge, Jr. et al. | .. | 340/365 A |
| 4,916,169 A | * | 4/1990 | Boardman et al. | ............. | 522/27 |

FOREIGN PATENT DOCUMENTS

| | | | |
|---|---|---|---|
| DE | 0 398 701 | | 11/1990 |
| EP | 0 146 307 | | 6/1985 |
| EP | 0 153 700 | | 9/1985 |
| EP | 0 238 033 | * | 9/1987 |
| EP | 0 358 452 | | 3/1990 |

OTHER PUBLICATIONS

S.D. Robinson, B.L. Shaw, *J.Chem.Soc.*, 1965, 1529.*

* cited by examiner

Primary Examiner—Susan W. Berman

(57) ABSTRACT

A process for the addition of compounds containing silicon-bonded hydrogen to compounds containing aliphatic unsaturation and compositions suitable for said process. The process is activated by actinic radiation and is conducted in the presence of a platinum complex having one cyclopentadienyl group that is eta-bonded to the platinum atom and three aliphatic groups that are sigma-bonded to the platinum atom and a free-radical photoinitiator that is capable of absorbing actinic radiation such that the hydrosilation reaction is initiated upon exposure to actinic radiation. The invention also provides compositions for use in the aforementioned process.

4 Claims, No Drawings

HYDROSILATION REACTION UTILIZING A (CYCLOPENTADIENE)(SIGMA-ALIPHATIC) PLATINUM COMPLEX AND A FREE RADICAL PHOTOINITIATOR

BACKGROUND OF THE INVENTION

1. Field of the Invention

This invention relates to a hydrosilation process involving the reaction of a compound containing silicon-bonded hydrogen with a compound containing aliphatic unsaturation in the presence of ultraviolet or visible radiation, and to compositions that are useful in that process. The invention further relates to polysiloxane compositions, prepared by that process, which compositions are useful for preparing dental impressions, adhesives, release liners, and caulking materials.

2. Discussion of the Art

Numerous patents teach the use of various complexes of cobalt, rhodium, nickel, palladium, or platinum as catalysts for accelerating the thermally-activated addition reaction (hydrosilation) between a compound containing silicon-bonded hydrogen and a compound containing aliphatic unsaturation. For example, U.S. Pat. No. 4,288,345 (Ashby et al) discloses as a catalyst for hydrosilation reactions a platinum-siloxane complex. U.S. Pat. No. 3,470,225 (Knorre et al) discloses production of organic silicon compounds by addition of a compound containing silicon-bonded hydrogen to organic compounds containing at least one non-aromatic double or triple carbon-to-carbon bond using a platinum compound of the empirical formula $PtX_2(RCOCR'COR'')_2$ wherein X is halogen, R is alkyl, R' is hydrogen or alkyl, and R'' is alkyl or alkoxy. The catalysts disclosed in the foregoing patents are characterized by their high catalytic activity. Other platinum complexes for accelerating the aforementioned thermally-activated addition reaction include: a platinacyclobutane complex having the formula $(PtCl_2-C_3H_6)_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alcohol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, Joy); a hexamethyl-dipyridine-diplatinum iodide (U.S. Pat. No. 3,567,755, Seyfried et al); a platinum curing catalyst obtained from the reaction of chloroplatinic acid and a ketone having up to 15 carbon atoms (U.S. Pat. No. 3,814,731, Nitzsche et al); a platinum compound having the general formula $(R')PtX_2$ where R' is a cyclic hydrocarbon radical or substituted cyclic hydrocarbon radical having two aliphatic carbon-carbon double bonds, and X is a halogen or alkyl radical (U.S. Pat. No. 4,276,252, Kreis et al); platinum alkyne complexes (U.S. Pat. No. 4,603,215, Chandra et al.); platinum alkenylcyclohexene complexes (U.S. Pat. No. 4,699,813, Cavezzan); and a colloidal hydrosilation catalyst provided by the reaction between a silicon hydride or a siloxane hydride and a platinum (0) or platinum (II) complex (U.S. Pat. No. 4,705,765, Lewis). Although these platinum complexes and many others are useful as catalysts in processes for accelerating the thermally-activated addition reaction between the compounds containing silicon-bonded hydrogen and compounds containing aliphatic unsaturation, processes for promoting the ultraviolet or visible radiation-activated addition reaction between these compounds are much less common. Platinum complexes that can be used to initiate ultraviolet radiation-activated hydrosilation reactions have been disclosed, e.g., platinum azo complexes (U.S. Pat. No. 4,670,531, Eckberg); ($\eta^4$-cyclooctadiene) diarylplatinum complexes (U.S. Pat. No. 4,530,879, Drahnak); and ($\eta^5$-cyclopentadienyl)trialkylplatinum complexes (U.S. Pat. No. 4,510,094, Drahnak). Other compositions that are curable by ultraviolet radiation include those described in U.S. Pat. Nos. 4,640,939 and 4,712,092 and in European Patent Application No. 0238033. However, these patents do not indicate that the platinum complexes disclosed therein would be useful for initiating a visible radiation-activated hydrosilation reaction. U.S. Pat. No. 4,916,169 describes hydrosilation reactions activated by visible radiation.

SUMMARY OF THE INVENTION

In one aspect, this invention provides an improved process for the actinic radiation-activated addition reaction of a compound containing silicon-bonded hydrogen with a compound containing aliphatic unsaturation, said addition being referred to as hydrosilation, the improvement comprising using, as a platinum hydrosilation catalyst, an ($\eta^5$-cyclopentadienyl)tri($\sigma$-aliphatic)platinum complex, and, as a reaction accelerator, a free-radical photoinitiator capable of absorbing actinic radiation, i.e., light having a wavelength ranging from about 200 nm to about 800 nm. The process can also employ, as a sensitizer, a compound that absorbs actinic radiation, and that is capable of transferring energy to the aforementioned platinum complex or platinum complex/free-radical photoinitiator combination, such that the hydrosilation reaction is initiated upon exposure to actinic radiation. The process is applicable both to the synthesis of low molecular weight compounds and to the curing of high molecular weight compounds, i.e., polymers, containing unsaturated groups, e.g.,

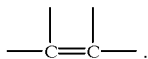

For example, the process comprises exposing to actinic radiation, i.e., radiation having a wavelength of about 200 nm to about 800 nm, a composition capable of undergoing hydrosilation comprising:

(a)

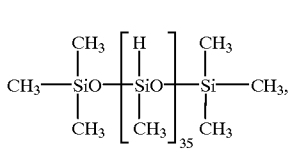

(b)

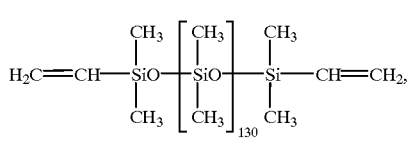

(c) a platinum complex catalyst having one cyclopentadienyl group that is eta-bonded to the platinum atom and three aliphatic groups that are sigma-bonded to the platinum atom, and (d) a free-radical photoinitiator capable of absorbing actinic radiation between 200 and 800 nm, such as:

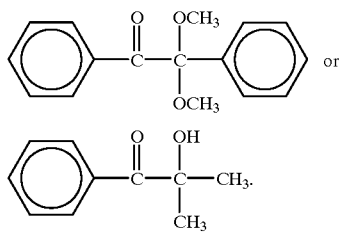

or

The composition can also contain a sensitizer capable of absorbing actinic radiation having a wavelength of about 200 nm to about 800 nm, such as:

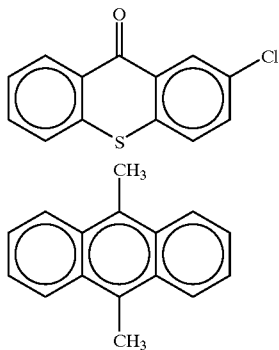

The invention further involves novel compositions, capable of undergoing hydrosilation, containing both the aforementioned platinum complex and the aforementioned free-radical photoinitiator. The compositions can also contain the aforementioned sensitizer.

Important applications of the process and compositions of the invention include adhesives, coatings, and light curable materials for dental applications, e.g., impressions.

The main advantage of using the free-radical photoinitiator in the actinic radiation-activated addition reaction of compounds containing silicon-bonded hydrogen with compounds containing aliphatic unsaturation is the unexpectedly high acceleration of the reaction, e.g., up to about a 40% reduction in curing time.

DETAILED DESCRIPTION

As used in this application, the term "compound", unless indicated otherwise, is a chemical substance which has a particular molecular identity or is made of a mixture of such substances, e.g., polymeric substances. The term "hydrosilation" means the addition of organosilicon compounds containing silicon-bonded hydrogen to a compound containing an aliphatic multiple bond, and in the hydrosilation process described in this application, it refers to those processes in which platinum-containing catalysts are used to effect the addition of an organosilicon compound having a silicon-bonded hydrogen atom to an aliphatically unsaturated compound having either olefinic or acetylenic unsaturation.

In a preferred embodiment of the invention, the platinum complex is an (η5 -cyclopentadienyl)tri(σ-aliphatic) platinum complex having the formula:

I wherein
Cp represents a cyclopentadienyl group that is <u>eta</u>-bonded to the platinum atom, the cyclopentadienyl group being unsubstituted or substituted with one or more groups that do not interfere in a hydrosilation reaction, and
each of $R^1$, $R^2$, and $R^3$ represents an aliphatic group having from one to eighteen carbon atoms, said $R^1$, $R^2$, and $R^3$ groups being sigma-bonded to the platinum atom.

The groups represented by $R^1$, $R^2$, and $R^3$ can be unsubstituted or substituted hydrocarbyl groups, or unsubstituted or substituted acyl groups, said substituents, if any, not interfering in a hydrosilation reaction. The groups can be straight-chain, branched-chain, and, if sufficiently large, cyclic.

($\eta^5$-Cyclopentadienyl)trimethylplatinum can be prepared by the addition of a solution of cyclopentadienylsodium in tetrahydrofuran to an equimolar amount of iodotrimethylplatinum dissolved in benzene, and isolation of the product complex from the reaction mixture according to the procedure of S. D. Robinson and B. L. Shaw, *J. Chem. Soc.*, 1965, 1529. Other ($\eta^5$ -cyclopentadienyl)trialiphaticplatinum complexes can be prepared by using corresponding amounts of substituted cyclopentadienylsodium in place of cyclopentadienylsodium and various trialiphatic platinum halides in place of iodotrimethylplatinum.

Representative examples of suitable ($\eta^5$-cyclopentadienyl)trialiphaticplatinum complexes useful in the practice of this invention include the following, in which (Cp) represents the ($\eta^5$-cyclopentadienyl) group:
(Cp)trimethylplatinum (Cp)ethyldimethylplatinum (Cp) triethylplatinum (Cp)triallylplatinum (Cp)tripentylplatinum (Cp)trihexylplatinum (methyl-Cp)trimethylplatinum (trimethylsilyl-Cp)trimethylplatinum (phenyldimethylsilyl-Cp)trimethylplatinum (Cp)acetyldimethylplatinum
Other suitable ($\eta^5$ -cyclopentadienyl)trialiphaticplatinum complexes suitable for this invention are described in U.S. Pat. No. 4,510,094, incorporated herein by reference.

Photoinitiators suitable for this invention are those compounds capable of generating free radicals upon absorption of actinic radiation between 200 and 800 nm and are preferably selected from the following classes of compounds: (1) monoketals of α-diketones or α-ketoaldehydes, and (2) acyloins and their corresponding ethers.

Monoketals of a-diketones and a-ketoaldehydes have the general formula:

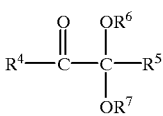

wherein $R^4$ preferably represents an aryl group that is unsubstituted or substituted with one or more groups that do not interfere with the hydrosilation reaction, and $R^5$, $R^6$, and $R^7$ each independently represents a member selected from the group consisting of an aryl group that is unsubstituted or substituted with one or more groups that do not interfere with the hydrosilation reaction, an aliphatic group having from one to eighteen carbon atoms, and hydrogen. Representative examples of these compounds are the commercially available derivatives "Irgacure" 651 (Ciba Geigy), for which $R^4$ and $R^5$ each represents the phenyl group, and R6 and $R^7$ each represents the methyl group, "Irgacure" 184 (Ciba Geigy), for which $R^4$ represents the phenyl group, $R^7$ represents hydrogen, and $R^5$ and $R^6$ together represent the group $-(CH_2)_5-$, and "DEAP" (Union Carbide Corp.), for which $R^4$ represents the phenyl group, $R^5$ represents hydrogen, and $R^6$ and $R^7$ each represents the ethyl group.

Acyloins and their corresponding ethers have the general formula:

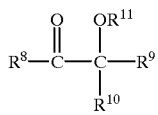

wherein $R^6$ preferably represents an unsubstituted aryl group or an aryl group substituted with one or more groups that do not interfere with the hydrosilation reaction, and $R^9$, $R^{10}$, and $R^{11}$ each independently represents a member selected from the group consisting of an aryl group that is unsubstituted or substituted with one or more groups that do not interfere with the hydrosilation reaction, an aliphatic group having from one to eighteen carbon atoms, and hydrogen. Representative examples of these compounds are the commercially available derivatives "Darocure" 1173 (EM Industries, Inc.), for which $R^8$ represents the phenyl group, $R^9$ and $R^{10}$ each represents the methyl group, and $R^{11}$ represents hydrogen, "Darocure" 1116 (EM Industries, Inc.), for which $R^8$ represents the 4-isopropylphenyl group, $R^9$ and $R^{10}$ each represents the methyl group, and $R^{11}$ represents hydrogen, and "Vicure" 30 (Stauffer Chemical Co.), for which $R^8$ and $R^9$ each represents the phenyl group, $R^{10}$ represents hydrogen, and $R^{11}$ represents the methyl group.

Sensitizers suitable for this invention are those compounds capable of absorbing actinic radiation within the ultraviolet and visible regions of the electromagnetic spectrum, i.e., about 200 nm to about 800 nm, and capable of transferring energy to the platinum complex. They must not inhibit the hydrosilation reaction. Sensitizers are preferably selected from two classes of compounds: 1) polycyclic aromatic compounds, and 2) aromatic compounds containing a ketone chromophore. The sensitizer compounds can be substituted with any substitutent that does not interfere with the light absorbing and energy transferring capabilities of the sensitizer compound or the hydrosilation catalyst. Examples of typical substituents include alkyl, alkoxy, aryl, aryloxy, aralkyl, alkaryl, halogen, etc. Representative examples of polycyclic aromatic sensitizers suitable for the invention include anthracene, 9-vinylanthracene, 9,10-dimethylanthracene, 9,10-dichloroanthracene, 9,10-dibromoanthracene, 9,10-diethylanthracene, 9,10-diethoxyanthracene, 2-ethyl-9,10-dimethylanthracene, naphthacene, pentacene, benz[a]anthracene, 7,12-dimethylbenz[a]alanthracene, azulene, and the like.

Some of the foregoing examples are illustrated below:

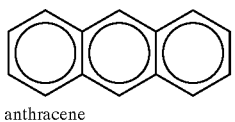

anthracene

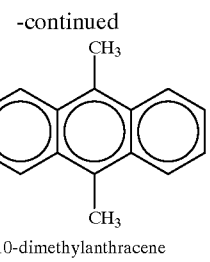

9,10-dimethylanthracene

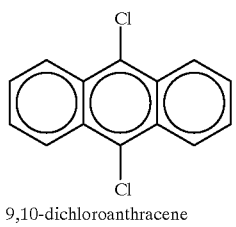

9,10-dichloroanthracene

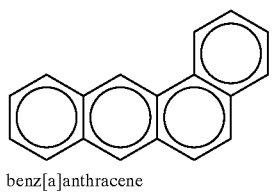

benz[a]anthracene

Representative examples of aromatic ketone sensitizers suitable for this invention include 2-chlorothioxanthone, 2-isopropylthioxanthone, thioxanthone, anthraquinone, benzophenone, 1-chloroanthraquinone, bianthrone, and the like. Some of the foregoing examples are illustrated below:

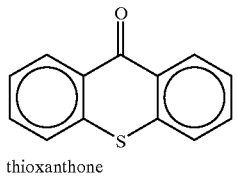

thioxanthone

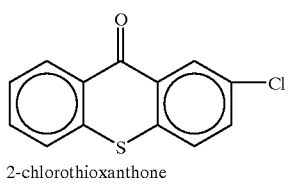

2-chlorothioxanthone

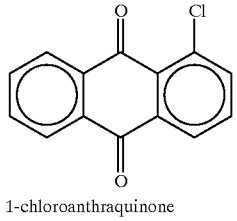

1-chloroanthraquinone

Turning now to the reactants to be used in the radiation-activated addition reaction, compounds containing aliphatic unsaturation which are useful in the present invention have olefinic or acetylenic unsaturation. These compounds are well-known in the art of hydrosilation and are disclosed in such patents as U.S. Pat. No. 3,159,662 (Ashby), U.S. Pat. No. 3,220,972 (Lamoreaux), and U.S. Pat. No. 3,410,886 (Joy), which disclosures of said compounds are incorporated herein. In instances where these unsaturated compounds contain elements other than carbon and hydrogen, it is preferred that these elements be either oxygen, nitrogen, silicon, a halogen, or a combination thereof. The aliphatically unsaturated compound can contain one or more carbon-to-carbon multiple bonds. Representative examples of the aliphatically unsaturated hydrocarbons which can be employed include mono-olefins, for example, ethylene, propylene, and 2-pentene; diolefins, for example, divinylbenzene, butadiene, and 1,5-hexadiene; cycloolefins, for example, cyclohexene and cycloheptene; and monoalkynes, for example, acetylene, propyne, and 1-buten-3-yne. The aliphatically unsaturated compounds can have up to 20 to 30 carbon atoms, or more.

Oxygen-containing aliphatically unsaturated compounds can also be used, especially where the unsaturation is ethylenic, such as methyl vinyl ether, divinyl ether, phenyl vinyl ether, monoallyl ether of ethylene glycol, allyl aldehyde, methyl vinyl ketone, phenyl vinyl ketone, acrylic acid, methacrylic acid, methyl acrylate, allyl acrylate, methyl methacrylate, allyl methacrylate, vinylacetic acid, vinyl acetate, and linolenic acid. Heterocyclic compounds containing aliphatic unsaturation in the ring, such as dihydrofuran, and dihydropyran, are also suitable for the present invention.

Halogenated derivatives of the previously mentioned aliphatically unsaturated compounds can be employed, including acyl chlorides as well as compounds containing a halogen substituent on a carbon atom other than a carbonyl carbon atom. Such halogen-containing compounds include, for example, vinyl chloride, and the vinyl chlorophenyl esters.

Unsaturated compounds containing nitrogen substituents such as acrylonitrile, N-vinylpyrrolidone alkyl cyanide, nitroethylene, etc., are also useful in the practice of the present invention.

Other unsaturated compounds useful in the practice of the present invention include polymers containing aliphatic unsaturation, such as the polyester resins prepared from polybasic saturated or unsaturated acids with polyhydric unsaturated alcohols, and the polyester resins prepared by reacting unsaturated polybasic acids with saturated polyhydric alcohols.

A particularly useful type of unsaturated compound which can be employed in the practice of the present invention is that containing silicon, such as those compounds commonly referred to as organosilicon monomers or polymers. These unsaturated organosilicon compounds have at least one aliphatically unsaturated organic radical attached to silicon per molecule. The aliphatically unsaturated organosilicon compounds include silanes, polysilanes, siloxanes, silazanes, as well as monomeric or polymeric materials containing silicon atoms joined together by methylene or polymethylene groups or by phenylene groups.

Preferred among the aliphatically unsaturated organosilicon compounds useful in the present invention are the monomeric silanes having the empirical formula $$R_b^{12}R_c^{13}SiX_{(4-b-c)} \qquad (II)$$

the cyclopolysiloxanes having the empirical formula $$(R^{12}R^{13}SiO)_d \qquad (II)$$

and the polyorganosiloxanes having the empirical formula $$R_e^{12}R_f^{13}SiO_{(4-e-f)/2} \qquad (IV)$$

wherein $R^{12}$ represents a monovalent aliphatic unsaturated hydrocarbyl group, $R^{13}$ represents a monovalent saturated hydrocarbyl group, x represents a hydrolyzable group, b represents an integer from 1 to 4, inclusive, c represents zero or an integer from 1 to 3, inclusive, the sum of b and c being 1 to 4, d represents an integer from 3 to 18, inclusive, e represents a number having a value of 0.0001 to 1, inclusive, and f represents zero or a number such that the sum of e and f is equal to 1 to 2, inclusive.

Monovalent aliphatic unsaturated hydrocarbyl groups represented by $R^{12}$ include alkenyl, for example, vinyl, propenyl, isopropenyl, 3-butenyl, and 5-hexenyl. Groups represented by $R^{13}$ include, for example, alkyl groups, such as methyl, ethyl, and pentyl; cycloalkyl groups, such as cyclopentyl and cyclohexyl; aryl groups such as phenyl and tolyl; aralkyl groups, such as benzyl and phenylethyl; and halogenated hydrocarbyl groups, such as haloalkyl, e.g., chloromethyl, trichloromethyl, and 3,3,3-trifluoropropyl, and haloaryl, e.g., chlorophenyl. Hydrolyzable groups represented by X include, for example, halogen groups such as chloro, bromo, and iodo; alkoxy groups such as methoxy, ethoxy, and phenoxy; and acyloxy groups such as acetoxy, propionoxy, and benzoyloxy. A hydrolyzable group is one which undergoes a displacement reaction with water.

In one particularly preferred embodiment of the process of the invention, the compound containing aliphatic unsaturation is an aliphatically unsaturated polyorganosiloxane represented by the general formula:

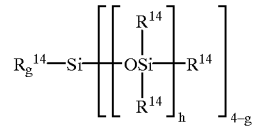

V wherein each $R^{14}$ can be the same or different and represents a non-halogenated or halogenated ethylenically-unsaturated group having from 2 to 18 carbon atoms, such as vinyl, propenyl, and chlorovinyl, a non-halogenated or halogenated alkyl group having from 1 to 18 carbon atoms, such as methyl, ethyl, propyl, hexyl, octyl, dodecyl, octadecyl, trichloromethyl, and 3,3,3-trifluoropropyl, a non-halogenated or halogenated cycloalkyl group having from 3 to 12 carbon atoms, such as cyclopentyl and cyclohexyl, or phenyl, at least 70% of all $R^{14}$ groups being methyl groups, but no more than 10% of all $R^{14}$ groups being vinyl or other alkenyl, e.g., having 3 to 18 carbon atoms, and at least one of the R14 groups being vinyl or other alkenyl, e.g., having 3 to 18 carbon atoms;

h represents a number having a value from 1 to about 3,000; and g represents 0, 1, 2, or 3.

The reactant containing the silicon-hydrogen linkage can be a polymeric compound or a compound that is not polymeric. These compounds are well-known in the art and are disclosed in the patents which describe the aliphatically unsaturated reactant, i.e., Ashby, U.S. Pat. No. 3,159,662; Lamoreaux, U.S. Pat. No. 3,220,972; and Joy, U.S. Pat. No. 3,410,886. The reactant containing the silicon-hydrogen linkage should contain at least one silicon-bonded hydrogen atom per molecule, with no more than three hydrogen atoms attached to any one silicon atom.

Some classes of compounds having a silicon-bonded hydrogen atom which can be used in the invention are organosilanes having the empirical formula:

$$(H)_j Si(R^{15})_k (X)_{(4-j-k)} \qquad \text{VI}$$

organocyclopolysiloxanes having the empirical formula:

$$(HR^{15}SiO)_d \qquad \text{VII}$$

and organohydrosiloxane polymers or copolymers having the empirical formula:

$$(R^{15})_f Si(H)_e O_{(4-e-f)/2} \qquad \text{VIII}$$

wherein $R^{15}$ represents an organic group, preferably selected from the group consisting of monovalent hydrocarbyl groups, and halogenated monovalent hydrocarbyl groups, j represents the integer 1, 2, or 3, k represents zero or an integer of 1 to 3, inclusive, the sum of j and k being equal to 1 to 4, and X, d, e and f are as defined above for formulas II, III, and IV.

Among the groups represented by $R^{15}$ include, for example, alkyl groups having 1 to 18 carbon atoms, e.g., methyl, ethyl, propyl, octyl, and octadecyl; cycloalkyl groups having 5 to 7 ring carbon atoms, e.g., cyclohexyl and cycloheptyl; aryl groups having 6 to 18 carbon atoms, e.g., phenyl, naphthyl, tolyl, xylyl; and combinations of alkyl and aryl groups, e.g., aralkyl groups, such as, benzyl and phenylethyl, and halo-substituted groups thereof, e.g., chloromethyl, chlorophenyl, and dibromophenyl. Preferably, the $R^{15}$ group is methyl or both methyl and phenyl. The $R^5$ group can also be an unsaturated aliphatic group having 1 to 20 carbon atoms, such as alkenyl or cycloalkenyl, e.g., vinyl, allyl and cyclohexenyl. When the $R^{15}$ group is a group with aliphatic unsaturation, the silicon compound containing silicon-hydrogen linkages can be reacted with itself to form a polymer.

Among the inorganic compounds which contain silicon-bonded hydrogen atoms and which are useful as reactants in the process of the present invention are included, for example, trichlorosilane, dibromosilane, pentachlorodisilane, pentachlorodisiloxane, and heptachlorotrisilane.

A preferred compound having silicon-bonded hydrogen useful in this invention is a polyorganohydrosiloxane having the general formula:

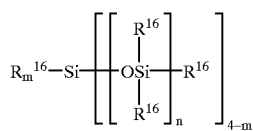

IX wherein each $R^{16}$ can be the same or different and represents hydrogen, an alkyl group having 1 to 18 carbon atoms, a cycloalkyl group having 3 to 12 carbon atoms, or a phenyl group, at least one but not more than one-half of all the $R^{16}$ groups in the siloxane being hydrogen, m represents 0, 1, 2, or 3, and n represents a number having an average value from 1 to about 3,000.

The hydrosilation composition useful in the synthesis of low molecular weight compounds by the process of the invention can be prepared by mixing about 0.1 to about 10.0 equivalent weights of the compound having silicon-bonded hydrogen with one equivalent weight of the compound having aliphatic unsaturation and then adding an amount of platinum complex catalyst sufficient to catalyze the reaction and an amount of a free-radical photoinitiator sufficient to accelerate the reaction. Optionally, an amount of a sensitizer sufficient to sensitize the platinum complex/free-radical photoinitiator combination upon exposure to actinic radiation having a wavelength from about 200 nm to about 800 nm can also be added. The amount of the catalyst can range from about 5 to about 1,000 parts by weight, preferably from about 50 to about 500 parts by weight, per 1,000,000 parts by weight of the total composition. The amount of free-radical photoinitiator can range from about 50 to about 50,000 parts by weight, preferably from about 100 to about 5,000 parts by weight, per 1,000,000 parts by weight of the total composition. The amount of sensitizer can range from about 50 to about 50,000 parts by weight, preferably from about 100 to about 5,000 parts by weight, per 1,000,000 parts by weight of the total composition.

Known techniques can be used to conduct the hydrosilation reaction. In carrying out a hydrosilation reaction in the practice of this invention, the reactants and catalyst can be introduced into a vessel equipped for stirring, where the mixture is stirred until it is homogenous. If either of the reactants is a solid or is extremely viscous, a solvent can be introduced into the vessel to facilitate uniform mixing of the reactants. Suitable solvents include aromatic hydrocarbons, such as xylene and toluene; aliphatic hydrocarbons, such as hexane and mineral spirits; and halogenated hydrocarbons, such as chlorobenzene and trichloroethane. It is desirable that the solvent be transmissive to actinic radiation. From about 0.1 to about 10 parts of solvent per part by weight of the combined reactants may be used. The resulting reaction product will generally be sufficiently pure for its intended use. However, it may be desirable to remove the solvent if one has been employed.

The hydrosilation compositions useful in the preparation of higher molecular weight cured siloxane polymers, by the process of this invention, can be prepared by mixing an aliphatically unsaturated polysiloxane and the compound having silicon-bonded hydrogen in such a proportion so as to provide about 0.1 to about 10.0 silicon-bonded hydrogen atoms per unsaturated group, and then adding from about 5 to about 1,000 parts by weight, preferably from about 50 to about 500 parts by weight of platinum complex catalyst and from about 50 to about 50,000 parts by weight, preferably from about 100 to about 5,000 parts by weight of a free-radical photoinitiator. Optionally, from about 50 to about 50,000 parts by weight, preferably from about 100 to about 5,000 parts by weight of sensitizer, per 1,000,000 parts by weight of the total composition, can be added. The reaction mixture can be mixed, as by stirring, blending, or tumbling, until it is homogeneous.

The thoroughly mixed composition can then be applied to a substrate by any suitable means, such as by spraying, dipping, knife coating, curtain coating, roll coating, or the like, and the coating cured by using conventional techniques for providing actinic radiation. It is preferred that curing be conducted by exposing the coated substrate to radiation having a wavelength of about 200 nm to about 800 nm. Depending on the particular silicone formulation, catalyst, free-radical photoinitiator, optional sensitizer, and intensity of the actinic radiation, curing can be accomplished in a period from less than one second to less than 30 minutes. Any radiation source emitting radiation above about 200 nm can be used. Examples of suitable radiation sources include tungsten halogen lamps, xenon arc lamps, mercury arc lamps, incandescent lamps, and fluorescent lamps. Particularly preferred sources of actinic radiation are tungsten halogen, xenon arc, and mercury arc lamps.

Various additives conventionally included in hydrosilation compositions can be included in the curable compositions, depending on the intended purpose of the composition. Fillers and/or pigments, such as chopped fibers, crushed polymers, talc, clay, titanium dioxide, and fumed silica can be added. Soluble dyes, oxidation inhibitors, and/or any material that does not interfere with the catalytic activity of the platinum complex and does not absorb actinic radiation at the absorption wavelength of the free-radical photoinitiator, or of the optional sensitizer, can be added to the composition.

The shelf life of the curable compositions containing the catalyst and sensitizer can be extended by the addition of a conventional catalyst inhibitor. The amount of catalyst inhibitor can vary from about 1 to about 10 times, or more, the amount of platinum complex, depending on the activity of the particular complex or complex-accelerator used and the shelf life desired for the composition. Greater amounts of inhibitor should be used with the more active complexes, with lesser amounts being used for the less active complexes. Hydrosilation inhibitors are well known in the art and include such compounds as acetylenic alcohols, certain polyolefinic siloxanes, pyridine, acrylonitrile, organic phosphines and phosphates, unsaturated amides, and alkyl maleates.

The hydrosilation compositions of this invention can be applied to the surface of any solid substrate for a variety of purposes. Examples of such substrates include paper, cardboard, wood, cork, plastic, such as polyester, nylon, polycarbonate, etc., woven and nonwoven fabric, such as cotton, polyester, nylon, etc., metal, glass, and ceramic.

It is often advantageous to prime the surface of nonporous substrates to which the hydrosilation composition is to be applied to improve the adhesion of the composition to the substrate. Many primers and priming techniques (e.g., corona treatment) are described in the art and should be chosen on the basis of the substrate to be used. For example, the epoxy-functional siloxanes as taught in U.S. Pat. No. 4,243,718 (Murai et al) are useful for priming the surface of plastic films such as polyester and polyvinylchloride.

Compositions of this invention can be applied and cured in relatively thick sections, such as an impression material for dental applications or a fast-setting caulking material.

Advantages of this invention are further illustrated by the following examples, where the parts referred to are parts by weight. The particular materials and amounts recited as well as other conditions and details given should not be construed to unduly limit this invention.

Compositions of this inventions were evaluated for cure speed in the following manner.

Molds made from a 1.5 mm thick "Teflon" sheet with a 6 mm diameter hole through the sheet were clamped to clean glass slides so that the central axis of the hole in the mold was normal to the glass slide. The hole was filled with a sample of the composition being evaluated. A "Visilux" 2 dental curing light (available from Minnesota Mining and Manufacturing Company) with a light output in the visible region of the spectrum between 400 and 500 nm was clamped to a ring stand and positioned such that the cylindrical tip of the light source was 5.0 mm above the top of the "Teflon" mold. The center of the 6 mm diameter sample was directly beneath the light tip. The sample was irradiated with the "Visilux" 2 light until a tack-free, cohesive silicone polymer was obtained as determined with a metal probe. Compositions were evaluated for cure speed under ultraviolet radiation by placing small samples of each formulation in shallow 2 inch diameter aluminum pans and irradiating the samples at a distance of 25 cm under a bank of six Sylvania 15 Watt "Black Light" bulbs or at a distance of 5 mm from a Caulk/Hanovia "Black Light", each with a maximum intensity output at 365 nm. All samples were tested in duplicate or triplicate.

EXAMPLE 1

A stock composition was prepared by mixing in a glass container 85 parts by weight of vinyl terminated polydimethylsiloxane polymer having the formula:

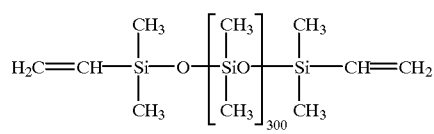

and 15 parts by weight of a compound containing silicon-bonded hydrogen atoms having the formula:

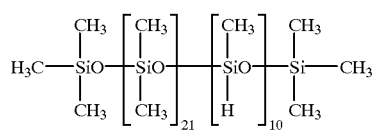

To 10.0 g portions of this stock composition were added the photohydrosilation catalyst $CpPt(CH_3)_3$ at a concentration of 960 ppm platinum and a photoinitiator selected from "Irgacure" 651, "Irgacure" 184, "Darocure" 1173, and "Daracure" 1116 at a concentration of 1,000 ppm. Compositions were irradiated as previously described, and the times until gelation of these compositions are set forth in Table I.

TABLE I

| | Gel time (sec) | |
|---|---|---|
| Photoinitiator | Ultraviolet ("Black Light") | Visible ("Visilux"2) |
| — | 123 | 162 |
| "Irgacure" 651 | 118 | 107 |
| "Irgacure" 184 | 113 | 116 |
| "Darocure" 1173 | 111 | 136 |
| "Darocure" 1116 | 101 | 108 |

The results in Table I indicate that several photoinitiators are capable of increasing the speed of a hydrosilation reaction.

EXAMPLE 2

To each of four 2 g portions of the stock composition of Example 1 in glass vials were added 960 ppm platinum in the form of CpPt(CH$_3$)$_3$ and from 0 to 4,000 ppm of the photoinitiator "Darocure" 1173. Compositions were irradiated as previously described, and gelation times of each composition are set forth in Table II.

TABLE II

| Amount of photoinitiator (ppm) | Gel time (sec) | |
|---|---|---|
| | Ultraviolet (Caulk/Hanovia) | Visible ("Visilux"2) |
| — | 240 | 143 |
| 1333 | 137 | 130 |
| 2666 | 137 | 124 |
| 4000 | 143 | 118 |

The data in Table II show that the rate of cure increases with increasing amounts of "Darocure" 1173 photoinitiator under a source of visible light up to a level of at least 4,000 ppm and under a source of ultraviolet light to a level of approximately 1,333 ppm.

EXAMPLE 3

To each of four compositions prepared as described in Example 2 were added 960 ppm platinum in the form of CpPt(CH$_3$)$_3$ and 1,000 ppm of the photosensitizer 2-chlorothioxanthone. Samples were irradiated as previously described, and the time until gelation of these compositions is set forth in Table III.

TABLE III

| Amount of photosensitizer (ppm) | Amount of photoinitiator (ppm) | Gel time (sec) | |
|---|---|---|---|
| | | Ultraviolet (Caulk/Hanovia) | Visible ("Visilux" 2) |
| — | — | 240 | 143 |
| 1,000 | — | 162 | 40 |
| 1,000 | 1,333 | 164 | 38 |
| 1,000 | 2,666 | 155 | 35 |
| 1,000 | 4,000 | 134 | 25 |

The data in Table III show that the addition of 2-chlorothioxanthone results in a significant enhancement of cure speed relative to that of the unsensitized compositions. Further enhancement can be achieved upon addition of "Darocure" 1173 photoinitiator up to a level of at least 4,000 ppm under a source of either ultraviolet or visible light.

EXAMPLE 4

A stock composition was prepared by mixing in a glass container 97.5 parts by weight of a vinyl-terminated polydimethylsiloxane having the formula:

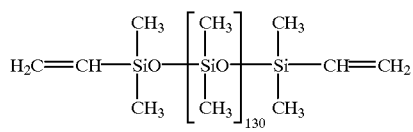

and 2.5 parts by weight of a compound containing silicon-bonded hydrogen having the formula:

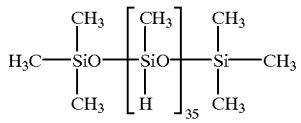

To 10.0 g aliquots of this composition were added CpPt(CH$_3$)$_3$ to the extent of from 50 to 500 ppm Pt and varying amounts of a photoinitiator selected from "Irgacure" 651, "Irgacure" 184, "Darocure" 1173, and "Darocure" 1116. Samples were irradiated as previously described, and the time until gelation of these compositions is set forth in Table IV.

TABLE IV

| Photoinitiator | Amount (ppm) | Amount of catalyst (ppm) | Gel time (sec) | |
|---|---|---|---|---|
| | | | Ultraviolet ("Black Light") | Visible ("Visilux"2) |
| — | — | 50 | 130 | 130 |
| — | — | 200 | 70 | 75 |
| — | — | 500 | 60 | 60 |
| "Irgacure" 651 | 500 | 50 | 250 | >300 |
| | 500 | 500 | 50 | 40 |
| | 100 | 200 | 65 | 69 |
| | 100 | 500 | 52 | 57 |
| "Irgacure" 184 | 500 | 500 | 55 | 49 |
| | 100 | 500 | 53 | 59 |
| "Darocure" 1173 | 500 | 500 | 53 | 46 |
| | 100 | 500 | 52 | 60 |
| "Darocure" 1116 | 500 | 500 | 50 | 48 |
| | 100 | 500 | 52 | 56 |

The data in Table IV show that the greatest increase in cure speed is observed when the catalyst and photoinitiator are present in approximately equal amounts.

EXAMPLE 5

This example illustrates the release characteristics of coatings prepared with the compositions of this invention. To a 30.0 g aliquot of the stock composition of Example 2 were added 9.4 mg of CpPt(CH$_3$)$_3$ (200 ppm Pt), 15 mg of 2-chlorothioxanthone (500 ppm), and 15 mg of "Irgacure" 651 photoinitiator (500 ppm). The composition was coated on super calendered Kraft paper at a coating weight of 1 to 2 g/m$^2$ and cured by irradiation under an atmosphere of nitrogen in a PPG processor that advanced the sample at a rate of 50 cm/sec under two medium pressure mercury lamps emitting 120 watts of radiation per centimeter of lamp length and subsequent heating in a circulating air oven at 100° C. for 2 minutes. Similarly coated samples that were not exposed to radiation did not cure when heated at 100° C.

The release value of the cured silicone coating was determined by the following procedure: A heptane-isopropyl alcohol solution of pressure-sensitive adhesive comprising isooctyl acrylate (95.5% by weight)-acrylic acid (4.5% by weight) copolymer, as described in Example 5 of U.S. Pat. No. Re. 24,906, incorporated herein by reference, was applied to the cured silicone coating and dried for 5 minutes at 70° C. in a circulating air oven to give a dry coating weight of 32 g/m$^2$. A biaxially oriented film of polyethylene terephthalate (PET) (38 micrometers thick) was pressed against the surface of the coating to produce a laminate consisting of a pressure-sensitive adhesive tape and a silicone-coated substrate. The laminate was cut into 2.5×25 cm strips. An average value of 15 g per 2.5 cm of width was measured to be the force required to pull the PET film with adhesive attached thereto (i.e., a pressure-sensitive adhesive tape) away from the silicone-coated substrate at an angle of 180° and a pulling speed of 230 cm/min.

The readhesion value of the pressure-sensitive tapes was determined by the following procedure: The pressure-sensitive tapes, as removed from the silicone coated surface, were applied to the surface of a clean glass plate. An average value of 1,400 g per 2.5 cm of width was measured to be the force required to pull the tape from the glass surface at an angle of 180° and a pulling speed of 230 cm/min. A control readhesion value was obtained for the pressure-sensitive tape by applying the tape, which had not been placed in contact with a silicone-coated surface, to a clean glass plate and measuring the force required to remove the tape from the plate. The control readhesion value was 1,500 g per 2.5 cm of width.

EXAMPLE 6

This example illustrates the preparation of a silicone-based pressure-sensitive adhesive tape from a composition of this invention. A mixture of the following three ingredients was prepared:

(1) 13.6 g of a dimethylvinylsiloxy endblocked polydimethylsiloxane containing an average of 25.1 dimethylsiloxane units per molecule;

(2) 25.6 g of a dimethylhydrogensiloxy endblocked polydimethylsiloxane containing an average of 28.7 dimethylsiloxane units per molecule; and (3) 100.0 g of a 60 percent by weight solution in xylene of a resinous organosiloxane copolymer comprising $CH_3SiO_{1/2}$, $SiO_{5/2}H$ and $SiO_{4/2}$ units in a ratio of 41.6:10.5:47.6. The copolymer exhibited a number average molecular weight, determined by gel permeation chromatography, of about 2,600 and a dispersity index of 2.6.

The mixture was stripped of volatile material by heating at 65° C. under less than 0.5 mm of Hg pressure on a rotary evaporator. To the resulting viscous mixture were added 0.80 g of 1,3,5,7-tetravinyltetramethylcyclotetra-siloxane, 2.0 g of toluene, 78 mg of $CpPt(CH_3)_3$ (500 ppm Pt), 100 mg of 2-chlorothioxanthone (1,000 ppm), and 100 mg of "Irgacure" 651 photoinitiator (1,000 ppm). The composition was knife coated at a thickness of 0.05 mm on a 0.05 mm thick polyethylene terephthalate film, and the coating was cured by irradiation under an atmosphere of nitrogen in a PPG processor that advanced the sample at a rate of 50 cm/sec under two medium pressure mercury lamps emitting 120 watts of radiation per centimeter of lamp length and subsequent heating in a circulating air oven at 100° C. for two minutes.

Adhesion was determined essentially according to the procedure described in ASTM D-330 (1983). Strips of the tape 2.54 cm wide and approximately 25 cm long were adhered to a glass surface using a 2.04 kg rolled weight. An average value of 1,600 g per 2.5 cm of width was measured to be the force required to pull the adhesive tape away from the glass surface at an angle of 180° and a pulling speed of 230 cm/min.

Shear strength was determined essentially according to the procedure described in ASTM D-3654 (1982). Specimens 1.27 cm wide and approximately 8 cm long were adhered to a bright annealed steel surface with an overlap area of 1.27 cm by 1.27 cm. The samples were suspended vertically and maintained at a temperature of 70° C. for one hour. A 1 kg weight was suspended from the free end of each specimen, and an average of 200 minutes was measured as the elapsed time before the adhesive bond failed while being maintained at a temperature of 70° C. The test was repeated at room temperature, and an average holding time exceeding 10,000 minutes was measured.

The tack of the adhesive tape was measured qualitatively by touching the cured adhesive with a finger. Tack was judged to be moderate.

EXAMPLE 7

This example illustrates the preparation of a conformal coating for electronic components using a composition of this invention. A composition consisting of the following ingredients in the amounts indicated was prepared:

| Ingredient | Amount (parts by weight) |
| --- | --- |
| Vinyl siloxane polymer[1] | 54.2 |
| Crosslinking Agent (PMC 54, available from Minnesota Mining and Manufacturing Company) | 30.8 |
| Catalyst $(CpPt(CH_3)_3)$ | 0.031 |
| Sensitizer (2-chlorothioxanthone) | 0.050 |
| Photoinitiator ("Irgacure" 651) | 0.050 |
| Fumed silica ("Quso", available from Degussa Corporation) | 15.0 |

[1] 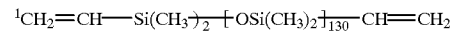 $CH_2 = CH - Si(CH_3)_2 - [OSi(CH_3)_2]_{130} - CH = CH_2$

The ingredients were introduced into a 250 ml beaker and mixed thoroughly. The mixture was transferred to a 50 cc syringe and degassed under reduced pressure for approximately 30 minutes to yield a bubble-free mixture.

The composition was applied to an integrated circuit board measuring 2 inches by 2 inches in sufficient quantity to provide a coating approximately 1 mm in thickness. The coating was irradiated with a "Visilux" 2 light source for approximately 4 minutes to provide a tough, elastomeric, transparent coating that adhered well to the circuit board.

EXAMPLE 8

This example illustrates preparation of a dental impression by means of a visible-light curable wash material and a chemically curable tray material.

A polyvinylsiloxane formulation curable by visible light was prepared by mixing the following ingredients in the amounts indicated:

| | Amount | |
| --- | --- | --- |
| Indegredient | (g) | (wt %) |
| Vinyl-terminated polysiloxane polymer of Example 1 | 8.5 | 76.81 |
| Crosslinking agent of Example 1 | 1.5 | 13.56 |
| Catalyst $(CpPt(CH_3)_3)$ | 0.015 | 0.14 |
| Sensitizer (2-chlorothioxanthone) | 0.01 | 0.09 |
| Photoinitiator ("Darocure" 1173) | 0.04 | 0.36 |
| Fumed Silica ("Aerosol" R-972, available from Degussa) | 1.0 | 9.04 |
| | 11.065 | 100.00 |

The first four ingredients were premixed; then fumed silica was added. The resultant mixture was painted on the entire surface of a single tooth of a typodont. The coated surface was then irradiated by means of a "Visilux" 2 light over the entire surface for approximately two minutes or until the resin was completely tack-free. Immediately following the irradiation step, a two-part chemically curable impression material (Express Medium Viscosity Wash, Minnesota Mining and Manufacturing Company, St. Paul, Minn.) was applied by syringe directly over the several teeth both adjacent to and including those previously irradiated with light. The material was allowed to set for about five minutes. The bulk material was easily removed from the typodont by firmly holding the typodont in one hand and the impression in the other. Upon removal of the silicone impression, it was observed that the light-cured material was firmly and completely bonded to the chemically-cured material. The stone model that was prepared from the impression showed improved detail where the light cured material was placed.

Various modifications and alterations of this invention will become apparent to those skilled in the art without departing from the scope and spirit of this invention, and it should be understood that this invention is not to be unduly limited to the illustrated embodiments set forth herein.

What is claimed is:

1. Radiation-curable composition comprising:

(a) a polyorganohydrosiloxane having the general formula:

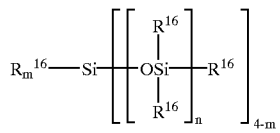

wherein each $R^{16}$ can be the same or different and represents an alkyl group, an cycloalkyl group, a phenyl group, or hydrogen, at least two but no more than one-half of all the $R^{16}$ groups in the siloxane being hydrogen, m represents 0, 1, 2, 3, and n represents a number having an average value from one to about 3000, (b) a polyorganosiloxane having the general formula:

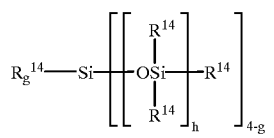

wherein each $R^{14}$ can be the same or different and represents a non-halogenated or halogenated ethylenically unsaturated group, a non-halogenated or halogenated alkyl group or cycloalkyl group, or the phenyl group, at least 70% of all $R^{14}$ group being methyl groups, but no more than 10% of all $R^{14}$ groups being vinyl or other alkenyl, h represents a number having a value from 1 to about 3000, and g represents 0, 1, 2, 3, (c) a platinum complex represented by the formula:

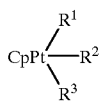

wherein

Cp represents a cyclopentadienyl group that is eta-bonded to the platinum atom, the cyclopentadienyl group being unsubstituted or substituted with one or more groups that do not interfere in a hydrosilation reaction, and each of $R^1$, $R^2$, and $R^3$ represents an aliphatic group having from one to eighteen carbon atoms, said $R^1$, $R^2$, and $R^3$ groups being sigma-bonded to the platinum atom, (d) a free-radical photoinitiator that is capable of absorbing actinic radiation and has the general formula:

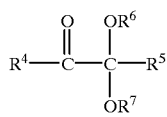

wherein $R^4$ represents an unsubstituted aryl group or an aryl group substituted with one or more groups that do not interfere with the hydrosilation reaction, $R^5$, $R^6$, and $R^7$ each independently represents a member selected from the group consisting of unsubstituted aryl groups and aryl groups substituted with one or more groups that do not interfere with the hydrosilation reaction, aliphatic groups having one to eighteen carbon atoms, and hydrogen.

2. The composition of claim 1, further including a sensitizer.

3. Radiation-curable composition comprising (a) a polyorganohydrosiloxane having the general formula:

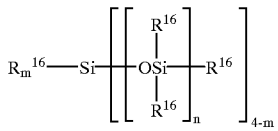

wherein each $R^{16}$ can be the same or different and represents an alkyl group, a cycloalkyl group, a phenyl group, or hydrogen, at least two but no more than one-half of all the $R^{16}$ groups in the siloxane being hydrogen, m represents 0, 1, 2 or 3, and n represents a number having an average value from one to about 3000, (b) a polyorganosiloxane having the general formula:

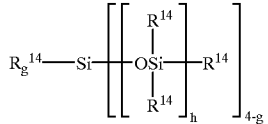

wherein each $R^{14}$ can be the same or different and represents a non-halogenated or halogenated ethylenically unsaturated group, a non-halogenated or halogenated alkyl group or cycloalkyl group, or the phenyl group, at least 70% of all $R^{14}$ group being methyl groups, but no more than 10% of all $R^{14}$ groups being vinyl or other alkenyl, and at least two of the $R^{14}$ groups being vinyl or other alkenyl, h represents a number having a value from 1 to about 3000, and g represents 0, 1, 2, or 3, (c) a platinum complex represented by the formula:

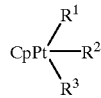

wherein

Cp represents a cyclopentadienyl group that is <u>eta</u>-bonded to the platinum atom, the cyclopentadienyl group being unsubstituted or substituted with one or more groups that do not interfere in a hydrosilation reaction, and each of $R^1$, $R^2$, and $R^3$ represents an aliphatic group having from one to eighteen carbon atoms, said $R^1$, $R^2$, and $R^3$ groups being sigma-bonded to the platinum atom, (d) a free-radical photoinitiator that is capable of absorbing actinic radiation and has the general formula:

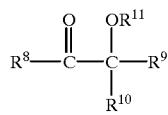

wherein $R^8$ represents an unsubstituted aryl group or an aryl group substituted with one or more groups that do not interfere with the hydrosilation reaction, and $R^9$, $R^{10}$, and $R^{11}$ each independently represents a member selected from the group consisting of unsubstituted aryl groups or an aryl group substituted with one or more groups that do not interfere with the hydrosilation reaction, an aliphatic group having from one to eighteen carbon atoms, and hydrogen.

4. The composition of claim 3, further including a sensitizer.

* * * * *